(12) United States Patent
Biron

(10) Patent No.: US 11,511,011 B2
(45) Date of Patent: Nov. 29, 2022

(54) METHOD FOR VALIDATING A STERILIZATION PROCESS COMPRISING TWO SUCCESSIVE CONTAMINATIONS

(71) Applicant: Jean-François Biron, Merignac (FR)

(72) Inventor: Jean-François Biron, Merignac (FR)

( * ) Notice: Subject to any disclaimer, the term of this patent is extended or adjusted under 35 U.S.C. 154(b) by 868 days.

(21) Appl. No.: 16/349,640

(22) PCT Filed: Nov. 15, 2017

(86) PCT No.: PCT/FR2017/000213
§ 371 (c)(1),
(2) Date: May 14, 2019

(87) PCT Pub. No.: WO2018/091788
PCT Pub. Date: May 24, 2018

(65) Prior Publication Data
US 2019/0343975 A1 Nov. 14, 2019

(30) Foreign Application Priority Data
Nov. 15, 2016 (FR) ...................................... 16.01614

(51) Int. Cl.
*C12Q 1/22* (2006.01)
*A61L 2/28* (2006.01)
*A61L 2/04* (2006.01)
*A61L 2/08* (2006.01)
*A61L 2/18* (2006.01)

(52) U.S. Cl.
CPC ........ *A61L 2/28* (2013.01); *A61L 2/04* (2013.01); *A61L 2/081* (2013.01); *A61L 2/087* (2013.01); *A61L 2/18* (2013.01); *A61L 2/186* (2013.01); *C12Q 1/22* (2013.01); *A61L 2202/14* (2013.01); *A61L 2202/23* (2013.01)

(58) Field of Classification Search
CPC ... A61L 2/28; A61L 2/04; A61L 2/081; A61L 2/087; A61L 2/18; A61L 2/186; A61L 2202/14; A61L 2202/23; A61L 2202/20; A61L 2202/24; G01N 35/00663; C12M 1/34; C12Q 1/22; C12Q 1/02
See application file for complete search history.

(56) References Cited

U.S. PATENT DOCUMENTS

| 5,035,858 | A * | 7/1991 | Held | B03B 9/061 |
| | | | | 422/291 |
| 6,428,746 | B1 | 8/2002 | Muscarella et al. | |
| 8,808,620 | B1 | 8/2014 | Chu et al. | |
| 10,010,636 | B2 * | 7/2018 | Henniges | A61L 2/26 |
| 10,258,706 | B2 * | 4/2019 | Henniges | A61L 2/24 |
| 2002/0119508 | A1 * | 8/2002 | Morrison | G01N 21/8483 |
| | | | | 435/27 |
| 2008/0095676 | A1 | 4/2008 | Andretta | |
| 2015/0147773 | A1 | 5/2015 | Franciskovich et al. | |
| 2015/0374868 | A1 * | 12/2015 | Bruce | A61L 2/26 |
| | | | | 422/119 |
| 2018/0000976 | A1 * | 1/2018 | Nowruzi | A61L 2/208 |
| 2019/0209725 | A1 * | 7/2019 | Henniges | A61L 2/26 |

FOREIGN PATENT DOCUMENTS

WO 2014159696 A1 10/2014

OTHER PUBLICATIONS

Article with English translation: Guyomard, Sylvie, "Suivi de la biocharge (Bioburden) des solutions steriles avant sterilisation en 2010", La Vague, vol. 30, Sep. 1, 2010, pp. 16-18, Retrieved from the Internet: URL:http://a3p.org/images/stories/article/scientifique/vague30/0pdf_articles/30pdf7.pdf, XP002772145.
International Search Report for PCT/FR2017/000213 dated Feb. 5, 2018.
Written Opinion for PCT/FR2017/000213 dated Feb. 5, 2018.
English Translation of the International Preliminary Report on Patentability for PCT/FR2017/000213 dated Oct. 11, 2018.
"Sterilization of health care products—Moist heat—Part 1: Requirements for the development, validation and routine control of a sterilization process for medical devices", National Standards Authority of Ireland, EN ISO 17665-1: 2006, Jan. 1, 2006, pp. 1-38, Retrieved from the Internet: URL: https://www.iso.org/standard/43187.html, XP055306730.
"European Pharmacopoeia 5.0", Jan. 1, 2005, Retrieved from the Internet: URL: http://library.njucm.edu.cn/yaodian/ep/EP5.0/index.html, XP002772264.
Boca, B M et al., "An Overview of the Validation Approach for Moist Heat Sterilization, Part I", Pharmaceutical Technology, Sep. 1, 2002, Retrieved from the Internet: URL: http://www.gmpua.com/Equipment/Sterility/Sterilization/article.pdf, XP055300049.
Guyomard, Sylvie, "Suivi de la biocharge (Bioburden) des solutions steriles avant sterilisation en 2010", La Vague, vol. 30, Sep. 1, 2010, pp. 16-18, Retrieved from the Internet: URL:http://a3p.org/images/stories/article/scientifique/vague30/0pdf_articles/30pdf7.pdf, XP002772145.

* cited by examiner

*Primary Examiner* — Regina M Yoo
(74) *Attorney, Agent, or Firm* — Pearne & Gordon LLP

(57) ABSTRACT

A method for validating a method for sterilizing an item, making it possible to validate the sterility assurance level achieved with this sterilization method. The method includes carrying out a first step of contaminating a container receiving the item with more than $10^5$ living microorganism cells, then carrying out a first sterilization cycle with the chosen method, then opening the container in order to contaminate it again with more than $10^5$ living microorganism cells, then carrying out a second sterilization cycle with the same method, and finally checking the sterility of the container after the first sterilization cycle and after the second sterilization cycle. The method is applicable in particular for products and devices intended for health use.

10 Claims, 2 Drawing Sheets

METHOD FOR VALIDATING A STERILIZATION PROCESS COMPRISING TWO SUCCESSIVE CONTAMINATIONS

TECHNICAL FIELD OF THE INVENTION

The present invention relates to a method for validating a sterilization process of a product, in particular a health product (medicine, medical device, cosmetic product, biotechnological product, etc.) packaged in a container that can be opened and then resealed, as well as an installation implementing such a validation process.

BACKGROUND OF THE INVENTION

The state of sterility of certain items and more particularly the state of sterility of items for health, particularly injectable products and the containers of these products, is a constant concern for those skilled in the art as for health authorities. The state of sterility is defined in different standards and regulatory texts in the form of a sterility assurance level, referred to by the acronym "SAL" (Sterility Assurance Level), which is the probability of the non-sterility of each sterilized item—whether a product or a container.

The selected sterility assurance level SAL generally imposes a statistical concentration below a threshold of $10^{-6}$ units forming a living colony, designated by the acronym "CFU" (colony-forming units), which corresponds to one living microorganism cell maximum for one million items, still a probability of non-sterility of one "chance" in a million for each sterilized item.

The sterilization processes can be divided into two categories according to the curves obtained:
  a) a first category of sterilization processes for which, according to some authors and a certain number of regulatory texts, it is possible to deduce an exponential decay curve of the number of living cells of microorganisms, depending on a parameter such as the exposure time or an applied irradiation dose; these processes consist in particular of sterilization by moist heat, by dry heat, by ethylene oxide, as well as by sterilization by beta or gamma irradiation,
  b) a second category of sterilization processes for which it is not possible to deduce an exponential decay curve of the number of living cells of microorganisms as a function of a parameter such as the exposure time or an applied dosage, which second category includes notably sterilization by hydrogen peroxide, by peracetic acid, or also by hydrostatic hyperpressure.

A first method for assessing the sterility assurance level SAL for sterilization processes in the first category uses biological indicators prepared with the defined microorganism or, if possible, the one proven to be the most difficult to destroy with the chosen sterilization process; these biological indicators are inoculated into samples of the item—product or container—to be sterilized. After the sterilization, the remaining number of living microorganism cells is measured by changing certain parameters of the sterilization process, most often the sterilization time or the dose, in order to be able to evaluate the interactions between the item and this process.

Through this method, a decay curve of the number of living microorganism cells is obtained according to several sterilization parameters, generally comprising the exposure time for sterilization processes using moist heat, or dry heat, or ethylene oxide, and including the dose received for beta or gamma irradiation sterilization processes.

For this first evaluation method, the curve is generally extended for very low levels of contamination, comprising statistically fewer than a single surviving microorganism cell, in order to deduce the characteristics of the sterilization process to achieve the sterility assurance level SAL sought.

However, this method is problematic because the extrapolation of the curve for very low levels of contamination is based on a hypothesis that experience cannot always prove. Some standards impose to reach a minimum correlation coefficient for high contamination values by measures that are indeed difficult to perform.

A second method for assessing the sterility assurance level SAL for sterilization processes of the second category involves inoculating items to be sterilized with biological indicators having a desired number of living cells of the microorganism, often between $10^3$ and $10^6$ cells, then, after the sterilization treatment, controlling the destruction of all living cells of these indicators.

For this method, a decay curve of the number of living microorganism cells as a function of a parameter, such as the exposure time or an applied sterilization dose or even the number of cells inoculated, cannot be calculated. The probability of non-sterility therefore cannot be assessed either, which poses problems of guaranteeing the SAL. In some cases, both the regulations and a person skilled in the art then consider that it is a decontamination without the need to reach the state of sterility.

GENERAL DESCRIPTION OF THE INVENTION

The aim of the present invention is in particular to avoid all the problems of the prior art described above.

It proposes for this purpose a method for validating a sterilization process of any item, for example a container or a product contained in a container adapted for the sterilization process under consideration. This method is applicable to all sterilization processes and aims primarily but not in a limiting manner to products and devices intended for health.

U.S. Pat. No. 6,428,746, published on Aug. 6, 2002, describes a method for validating a procedure for sterilizing an item, in particular a product intended for health, making it possible to validate the sterility assurance level achieved with this sterilization procedure, this procedure consisting in carrying out a single step of contamination of the item with more than $10^5$ living microorganism cells, then performing a sterilization cycle with the selected procedure and finally verifying the sterility of the item after the sterilization cycle.

According to the invention, the method for validating a process of sterilization of any item, allowing the sterility assurance level achieved with this sterilization process to be validated, is characterized in that it consists in performing a first step of contaminating a container receiving the item with more than $10^5$ living microorganism cells, then carrying out a first sterilization cycle with the selected sterilization process, then opening the container to contaminate it again with more than $10^5$ living microorganism cells, then carrying out a second sterilization cycle with the same process, and finally checking the sterility of the container after the first sterilization cycle and after the second sterilization cycle.

The validation method according to the invention may further comprise one or more of the following characteristics, which may be combined with each other.

Thus, advantageously, each contamination is carried out with at least $10^6$ living microorganism cells.

Advantageously, the contaminations are made with the living cells of the microorganism proven to be the most difficult to eliminate with the selected sterilization process.

Advantageously, the verification of the sterility of the container includes the detection of biological indicators demonstrating that none of these indicators has achieved growth.

Advantageously, the two contaminations are carried out under the same conditions, and the two cycles of sterilization are also performed under the same conditions, except as required due to the process and notably if the second cycle does not make it possible to destroy at least 5 logs of living cells of the microorganism most difficult to destroy by the sterilization process under consideration.

Advantageously, the validation method according to the invention makes it possible to modify the second sterilization cycle to ensure that the destruction of at least 5 logs of living cells of the microorganism most difficult to destroy by the sterilization process under consideration is actually achieved.

Advantageously, the invention makes it possible to carry out the operations of opening, re-contaminating, and closing the containers very rapidly in order to optimize the execution time of the routine cycles, composed of the first cycle, of a waiting time equal to these phases of opening, of recontamination and closure of these containers under the same environment conditions, and of the second cycle.

The objective of this method is to demonstrate a Sterility Assurance Level (SAL) of at least $10^{-5}$ for an initial contamination of $10^5$ living cells of the microorganism proven to be the most difficult to destroy by the sterilization process under consideration. This method is completely independent of the mode of operation of the sterilization process, and in particular of whether the sterilization process belongs to the first or second category mentioned above.

Obtaining such a SAL is based on obtaining a reduction of the contamination of at least 10 logs.

The present method is remarkable in that it actually proves these 10 logs of contamination reduction, which no method can achieve today. It involves inoculating the item to be sterilized with at least $10^5$ living cells of the microorganism advantageously proven to be the most difficult to destroy by the sterilization process under consideration, performing a first sterilization cycle which succeeds in destroying these at least $10^5$ living cells of this microorganism, then opening the containers, re-inoculating them with again at least $10^5$ living cells of the microorganism proven to be the most difficult to destroy by the sterilization process under consideration and closing them, then performing a second sterilization cycle identical to the first, which manages to destroy again at least $10^5$ living cells of the microorganism most difficult to destroy by this sterilization process.

The operations of opening the containers, re-inoculation, and re-closure are carried out by means of one of the devices according to the invention.

At the end of the first sterilization cycle, samples contaminated with $10^5$ CFU of the microorganism most difficult to destroy by the sterilization process under consideration are taken and subjected to a test known to the one skilled in the art and/or described in the regulatory texts for proving the destruction of these at least $10^5$ living cells of the microorganism. It is therefore proven at the end of this first cycle that the latter is capable of destroying 5 logs of contamination.

At the end of the second sterilization cycle, samples contaminated with $10^5$ living cells of the microorganism most difficult to destroy by the sterilization process under consideration are also taken and subjected to the same test known to the one skilled in the art and/or described in the regulatory texts for proving the destruction of these at least $10^5$ living cells of the microorganism most difficult to destroy by the sterilization process under consideration.

It is therefore proven at the end of this second cycle that the latter is capable of destroying at least 5 additional logs of living cells of the microorganism mentioned above.

The completion of this second cycle is essential because the container and the product or item it contains have already undergone a sterilization cycle, which cycle may have affected their characteristics and behavior during a new sterilization cycle. In the absence of a test, it is not possible to say that the second cycle, identical to the first one, actually destroys at least 5 additional logs of living cells of the microorganism that is the most difficult to destroy by the sterilization process under consideration.

In the case where the second cycle, for the reasons mentioned above, would not allow the reduction of at least 5 additional logs of living cells of this microorganism, the one skilled in the art could very well modify the characteristics of this second cycle to achieve this reduction of at least 5 logs.

The present method is remarkable in that it makes it possible to prove the destruction of at least 5 logs for the first cycle and at least 5 additional logs for the second cycle, which no method can achieve to date.

The present method is remarkable in that it makes it possible to demonstrate that the routine cycle composed of the first cycle, a waiting time in the same conditions as those experienced to open the containers, re-inoculate them, and close them again according to the invention, then of a second cycle, destroys at least 10 logs of the microorganism most difficult to destroy by the sterilization process under consideration.

As demonstrated above, a SAL of at least $10^{-5}$ is reached if the initial contamination before sterilization of the containers to be sterilized is less than or equal to $10^5$ CFU of the microorganism most difficult to destroy by the process sterilization under consideration, and that the sterilization process allows at least 10 logs of this microorganism to be destroyed.

The present method is remarkable in that it makes it possible to demonstrate this SAL of at least $10^{-5}$ if the initial contamination is less than $10^5$ cells of the microorganism most difficult to destroy by the sterilization process under consideration.

The invention also relates to an installation intended for implementing a validation method comprising any of the preceding characteristics, which installation comprises means for the successive displacement of the containers on a workstation comprising at least an opening system, inoculation means and at least one closure system of these containers.

According to a first embodiment of this installation, the at least one opening system, the inoculation means and the at least one closure system are arranged on a same location of the container.

According to another embodiment of the installation according to the invention, the at least one opening system, the inoculation means and the at least one closure system are arranged on container locations which are offset.

BRIEF DESCRIPTION OF THE DRAWINGS

The invention will be better understood and other features and advantages will emerge more clearly on reading the following description given by way of example and in a non-limiting manner, with reference to the appended drawings in which.

DESCRIPTION OF A PREFERRED EMBODIMENT OF THE INVENTION

Figure 1:
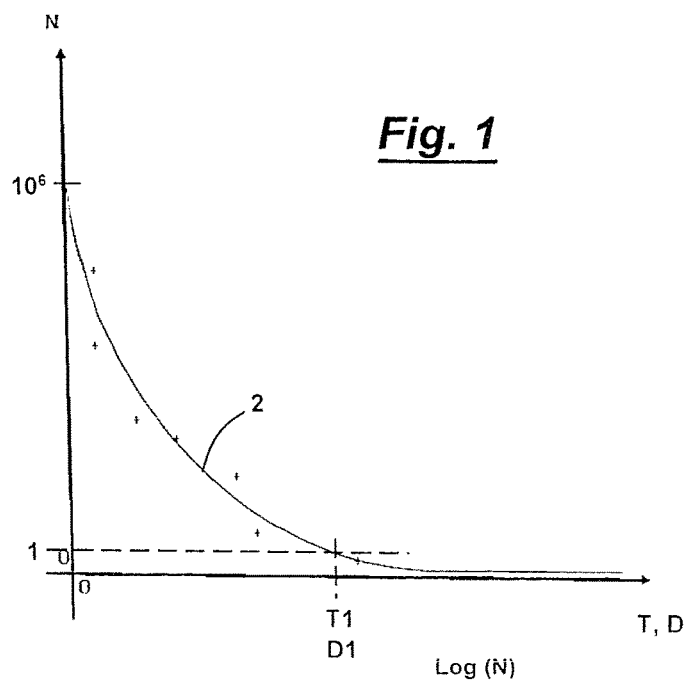
FIG. 1 is a graph showing a measurement curve of the number of living microorganism cells as a function of the exposure time or of the sterilization dose, for a sterilization process making it possible to establish an exponential decay curve.

FIG. 1 represents, for a sterilization process of the first category, a curve 2 yielding the number N of living microorganism cells measured after an exposure time T of the process or after a dose D in the case of treatment with irradiation, after having introduced a biological indicator comprising a quantity $N_0$ of living microorganism cells equal to $10^6$ in a closed container containing an item.

An exponential curve is obtained which tends towards zero for a rather long time T, or for a fairly strong dose D.

Alternatively, one can achieve the same type of curve for a sterilization process by inoculating the closed container with an N amount of living microorganism cells lower than $10^6$, similarly yielding an exponential decay curve depending on the quantity initially inoculated within this product.

Figure 2:
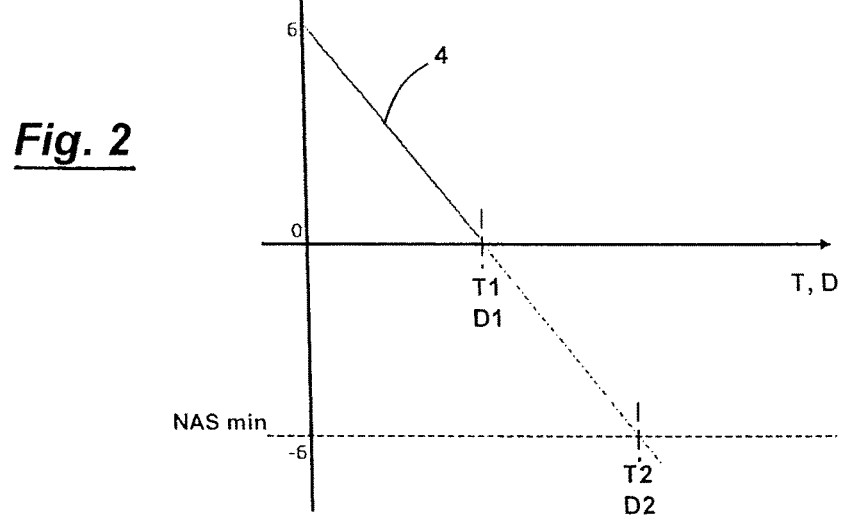
FIG. 2 is a graph showing the logarithmic conversion of this decay curve.

FIG. 2 represents, as a function of the exposure time T, or of the applied dose D, a straight line 4 calculated for the positive log (N) values, by the logarithmic conversion log (N) of the number N of living microorganism cells shown in FIG. 1. The line 4 starts at the time T=0 by the value log (N)=6 corresponding to the contamination by $10^6$ cells.

It will be noted with log (1)=0 that the logarithmic conversion of an exponential curve thus yields a straight line that passes through 0 at the time T1 (or at the dose D1) corresponding to the number N=1 representing a single living microorganism cell measured.

Various studies propose, according to a known validation method for these sterilization processes, the possibility of extrapolating the straight line in the negative log (N) values by continuing it below 0. These negative values correspond to a number N less than 1, i.e. to a probability of less than one surviving microorganism cell per treated container.

In particular, the European standard "NF EN556" relating to the sterilization of medical devices requires a probability of the presence of a microorganism cell of less than $10^{-6}$, i.e. a maximum risk of one chance per million that a sterilized item still contains surviving microorganisms, which is interpreted by some authors as equivalent to the probability of one living microorganism cell for one million sterilized items. From a contamination log (N)=6, it is therefore necessary to obtain a reduction of 12 logs giving the value log (N)=−6, which value is reached in principle at the necessary treatment time T2 or the dose D2.

In the case of an item initially comprising a higher or lower number of living microorganism cells, as the slope of the straight line given by the sterilization process remains the same, then a respectively longer or shorter time of exposure (or a higher or lower dose) is required to reach the value log (N)=−6.

In general, commonly used biological indicators contain a number of living microorganism cells between $10^6$ and $10^7$.

To avoid going down to negative log (N) values, one could start from a biological indicator presenting a very high level of contamination, for example equal to 12, to reach the final value equal to 0. However, this type of biological indicator is still not available on the market, at least for reference microorganisms used for sterilization processes.

It should be noted that the average initial contamination of a lot of medical devices or injectable products prepared for sterilization is generally low, often less than 10 living microorganism cells. However, this level of contamination may be random, and exceptional initial contamination cannot be ruled out, for example approaching the maximum level equal to $10^6$.

A problem posed by this validation method is that, since experience shows that certain standards impose a minimum correlation coefficient, it is sometimes difficult to establish the straight line 4 of logarithmic decay. Then, negative logarithmic values cannot be established and thus the required T2 exposure time or the D2 dose cannot be calculated.

Another problem with this validation method is that the extension of the straight line 4 to strongly negative values cannot be experimentally verified, and the margin of error remains unknown.

In particular for the log (N)=−6 value, one million units would have to be tested under identical conditions, which is not physically feasible. In particular, there is a problem of stability of the biological indicator, which would have to be placed in all items in a very short period of time in order to avoid its own evolution which would distort the test.

Moreover, it cannot be ruled out that, for the negative values of log (N), the law of evolution of the quantity of living microorganism cells would not be much more complex, as the mechanisms of destruction of these microorganisms have not been fully understood to date. These mechanisms depend in particular on the nature of the microorganisms, the sterilization process studied, and the interactions between the product to be sterilized and the types of microorganisms, which are often important.

Figure 3:
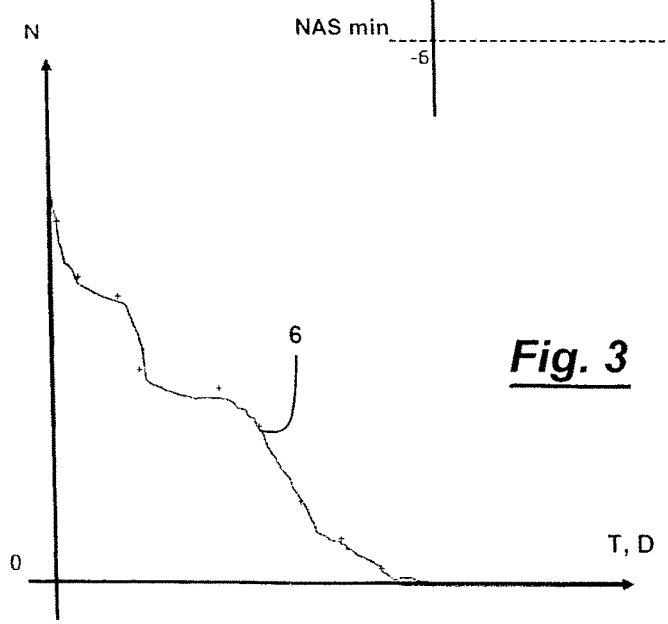
FIG. 3 is a graph showing a measurement curve of the number of living microorganism cells as a function of the exposure time or of the sterilization dose, for a sterilization process that does not yield an exponential decay curve.

FIG. 3 represents, for a sterilization process of the second category, a curve 6 yielding the number N of living microorganism cells measured after a time of exposure T of the process, after having introduced a biological indicator comprising a quantity of living microorganism cells equal to $10^6$ in a closed container containing an item.

A continuously descending curve 6 is obtained, which has no particular shape.

The texts presenting these sterilization methods of the second category provide for inoculating the items with biological indicators containing a defined number of living microorganism cells, often between $10^3$ and $10^6$, then for checking after sterilization that all indicators were destroyed.

Since it is impossible to establish a regular curve for measuring the number of cells from one parameter, we cannot calculate a probability of non-sterility for these processes. Moreover, in some cases, the regulations as well as the one skilled in the art consider that it is a decontamination without obligation to reach the state of sterility.

In addition, another problem posed by the set of validation methods presented above, with the notable exception of the method using a very high hydrostatic pressure, is that one can not treat a sterilization load homogeneously. In particular, for processes using dry heat, moist heat, or even ethylene oxide, there are systematically temperature differences in the load, and for the processes carrying out irradiation, differences in the dose are obtained between different points of the load.

There are then significant variations in sterility assurance that are frequently estimated at several logs of contamination reduction.

Figure 4:
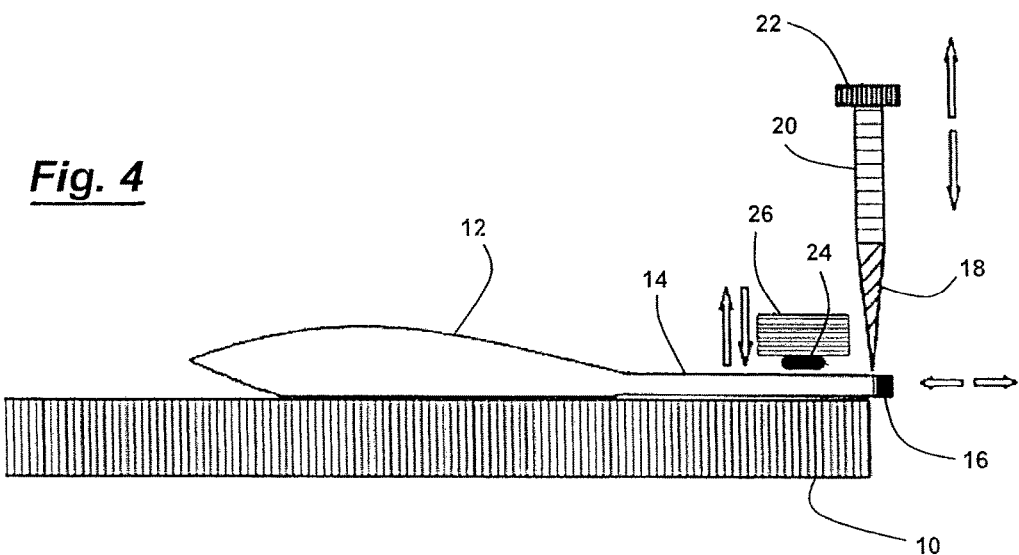
FIG. 4 shows in section, in a vertical plane perpendicular to the direction of travel, the workstation of an installation implementing a sterilization validation process according to the invention.
Figure 5:
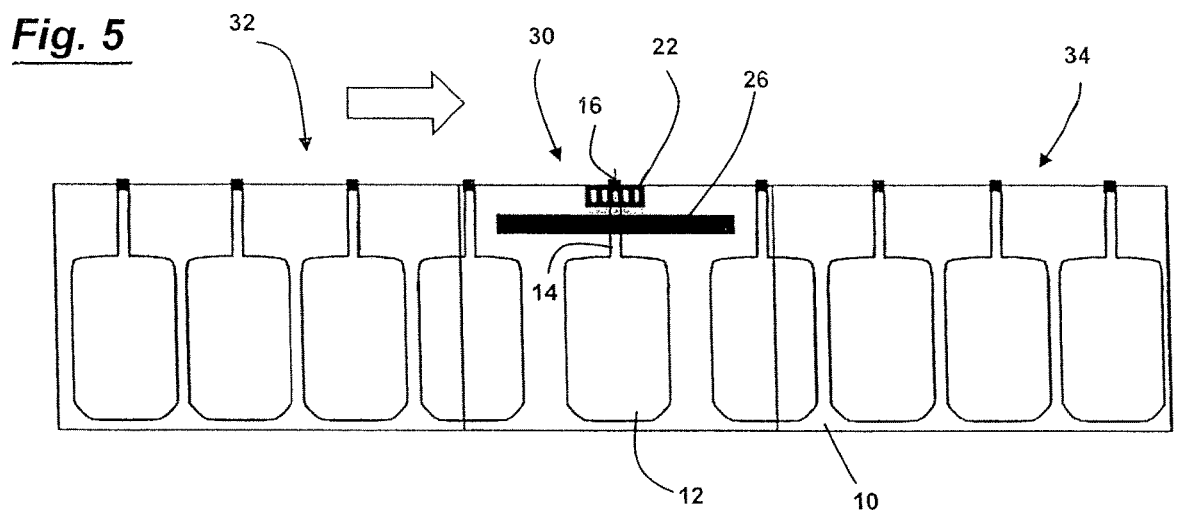
FIG. 5 is a top view of this installation according to the invention.

FIGS. 4 and 5 show an installation adapted for implementing the validation method according to the invention for any sterilization process, which may belong to the first as well as to the second category.

The installation comprises an elongated plate 10 receiving a succession of containers 12 aligned in the longitudinal direction, each containing a product to be sterilized. The container may have various shapes and sizes. The container may be in particular a pouch, a sachet, a rigid or flexible flask, a syringe, a rigid or flexible ampoule, a thermoformed tray, or any other container intended to contain any product to be sterilized. Among these products to be sterilized, we can cite in particular, but not exclusively, health products, and in particular medicines (chemical or biotechnological), medical devices, cosmetics, gene therapy products, advanced therapy drugs, grafting tissues and organs, food products, etc.

For simplicity in the description, the example given below will use a type of traditional container, namely a flexible pouch, containing a liquid product.

The advance of the pouches 12 in the longitudinal direction is performed step by step, by means of a manual or automated system.

The bags 12 have previously undergone a first sterilization cycle, after a first contamination carried out on one or more samples of items to be sterilized, with a number of living microorganism cells CFU of $10^6$ using preferentially a microorganism proven to be the most difficult to sterilize by the sterilization process studied.

The pouches 12 laid flat, and held on the plate 10 by a mechanical clamping device if necessary, have necks 14 arranged in parallel in the transverse direction, which necks are closed by a plug 16. The plate 10 comprises means for the longitudinal translation of the pouches 12 in a direction of advancing, such as a conveyor.

The plate 10 comprises a central work station 30 which is located between upstream pouches to be treated 32 and downstream pouches already treated 34. The workstation 30 keeps the pouch 12 being processed in the same position during the successive operations of opening, first or second contamination, and then closure of this pouch.

It will be noted that it is interesting to perform both contaminations under similar conditions, especially at the same workstation holding the pouch 12 in the same position, with an identical opening time, so as not to change the parameters allowing comparable effects to be obtained for these inoculations.

The plate 10 with its equipment fastened onto it can be arranged horizontally, or inclined in the transverse direction, in particular in a vertical plane, raising the neck 14 in order to prevent leakage of products when the pouches 12 are opened.

The plate 10 supports a cutting blade 18 fastened onto a vertical guide 20, cutting the neck 14 transversely closer to its plug 16 in order to modify as little as possible the interior volume of the container. The cutting blade 18 can be actuated either manually, by pressing on an upper support 22, or automatically for example with an electric actuator, comprising an electromagnet.

After the opening of the pouch 12 made by the cutting of its neck 14, the method comprises a contamination step that can be performed manually or automatically, for example with a syringe or a single or multiple pipette in the case where several pouches have been opened simultaneously.

The plate 10 supports a sealing device adapted for each type of pouch 12 after its neck 14 has been cut, such a device comprising a matrix 24 mounted below a descent system 26 which seals this neck as close as possible to the cut, this being also in order to limit the change in the internal volume and loss of microorganisms within it.

In particular, it is possible to carry out a sealing operation by resistance with continuous or discontinuous heating, by high frequency sealing, by a high inductance electromagnet or by any other system adapted to closing the pouch.

The descent system 26 can be operated manually or automatically, for example with an electric actuator with electromagnet. The descent system 26 is raised after sealing, to release the pouch 12 which can then move in the longitudinal direction.

After if necessary an opening of the mechanical clamping device of the pouch 12 on the plate 10, the set of pouches is moved longitudinally to place a new pouch on the workstation 30, and evacuate the downstream pouches towards the sterilizer with a handling that can be manual or automated. Advantageously, for the second sterilization the same pouches are placed in the sterilizer in the same place as for the first, and this being in order to obtain identical sterilization conditions.

After having arranged (for the first cycle) or replaced (for the second cycle) all the pouches 12 in the sterilizer, the sterilization cycle is started. After the first cycle, the biological indicators are revealed in order to verify that no indicator has grown, and the same is done after the second cycle.

The absence of growth following the first cycle proves that this cycle has destroyed at least $10^6$ spores of the microorganism most difficult to destroy by the sterilization process under consideration or, what is equivalent, that it has reduced the contamination by at least 6 logs of this microorganism.

The absence of growth following the second cycle also proves that this cycle reduces the contamination by at least 6 logs of this same microorganism.

Advantageously, the one skilled in the art can perform a second cycle different from the first one if this second cycle does not completely destroy the inoculated biological indicators, and therefore does not reduce the contamination by at least 6 logs. This can be explained in particular by changes in the product or the container due to the first cycle of sterilization.

The two cycles having been carried out in succession, the addition of the effects of the two cycles makes it possible to prove a reduction of the contamination of 6+6=12 logs of this microorganism, as indicated by the graph of FIG. 2 above. If the initial contamination of the item to be sterilized is not more than $10^6$ spores, the sterility assurance level SAL of $10^{-6}$ is reached after 12 contamination reduction logs as shown in FIG. 2.

A biological indicator is constituted of the microorganism most difficult to destroy by the sterilization process under consideration, and an initial contamination equal to $10^6$ spores of this microorganism corresponds to a very unfavorable case. Achieving a SAL sterility assurance level of $10^{-6}$ for an initial contamination of $10^6$ biological indicator spores corresponds to a situation described in reference texts as overkill conditions. The present validation tests described in the method according to the invention thus make it possible to guarantee that a SAL of $10^{-6}$ is achieved in all cases where the microbial contamination of the item to be sterilized is controlled to a reasonable level, compatible with that described in the bibliography and regulatory texts, that is to say significantly less than $10^6$ living microorganism cells, for a cocktail of microorganisms less resistant than spores of biological indicators.

Routinely, it is sufficient to reproduce identically the validation conditions composed of a first sterilization cycle, a waiting time under the conditions described during the validation tests (time, temperature, pressure, etc.), and a second sterilization cycle also identical to that performed during the validation tests. The whole of this sequence makes it possible to guarantee in a certain and proven way that a SAL of $10^{-6}$ is achieved if the initial contamination is less than or equal to $10^6$ spores. The whole of this sequence thus makes it possible to guarantee in a certain and proven way that this SAL of $10^{-6}$ is achieved if the initial contamination of the products to be sterilized is less than $10^6$ living microorganism cells, regardless of what microorganisms, since they are less resistant to the sterilization process than the spores.

Routinely, the pouches will not be contaminated for obvious reasons of health safety. The following cycle will be used: first sterilization, waiting time corresponding to the time required for the opening, the second inoculation and the closure of the pouches under conditions identical to those used in validation (time, temperature, pressure, etc.), second sterilization.

Figure 6:
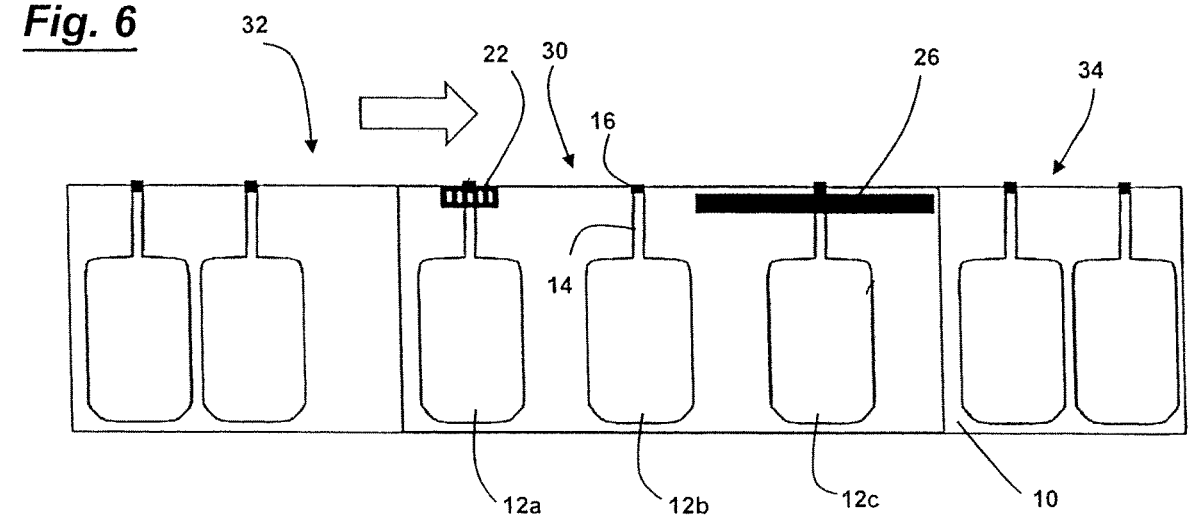
FIG. 6 is a top view of an installation according to the invention according to one variant embodiment.

FIG. 6 shows a plate 10 having a central workstation 30 receiving three pouches 12a, 12b, 12c offset longitudinally. The cutting operation on the first pouch 12a with the cutting blade 18, the inoculation on the second pouch 12b, and the sealing of the neck on the third pouch 12c are carried out simultaneously.

After this series of simultaneous operations, all the pouches 12 advance by one step in the longitudinal direction, in order to repeat the same operations on the following pouches. In this way, a productivity gain is achieved for the installation, in particular with automated cutting and sealing operations, because the three operations are performed simultaneously.

It goes without saying that the invention is not limited to the only preferred embodiments described above.

On the contrary, it embraces all the possible variants of embodiments, insofar as the latter do not go beyond the frame delimited by the appended claims which define the scope of the present invention.

Thus, the products or items to be sterilized may be other than products or health items, as long as it is advisable that they be subjected to sterilization. Similarly, the containers may be other than pouches when such containers are able to be opened by a cutting system and resealed immediately afterwards, all in a short time.

In any event, it is of course necessary that the installation according to the invention allows a rapid inoculation and closure of all the containers of a sterilization load, and this in order to minimize the overall time that passes between the two cycles of sterilization performed in validation.

What is claimed is:

1. A method of validation of a sterilization process of an item, in particular a product or a device intended for health, to validate a sterility assurance level achieved with the sterilization process, characterized in that the method consists in carrying out a first step of contaminating a container receiving the item with more than $10^5$ living microorganism cells, then carrying out a first sterilization cycle with the sterilization process, then opening the container to contaminate the container again with more than $10^5$ living microorganism cells, then carrying out a second sterilization cycle with the sterilization process, and finally checking a sterility of the container after the first sterilization cycle and after the second sterilization cycle.

2. The method of validation according to claim 1, characterized in that each contamination is carried out with at least $10^6$ living microorganism cells.

3. The method of validation according to claim 1, characterized in that the two contaminations are made with living microorganism cells proven to be the most difficult to eliminate with the sterilization process.

4. The method of validation according to claim 1, characterized in that the step of checking the sterility of the container includes a detection of biological indicators demonstrating that none of the biological indicators has achieved growth.

5. The method of validation according to claim 1, characterized in that the two contaminations are performed under identical conditions.

6. The method of validation according to claim 1, characterized in that the two sterilization cycles are performed under identical conditions.

7. The method of validation according to claim 1, characterized in that a routine cycle is composed of the first sterilization cycle, a waiting time and the second sterilization cycle.

8. The method of validation according to claim 7, characterized in that the waiting time of the routine cycle comprised between the two sterilization cycles is equal to a time required to contaminate the container between the first sterilization cycle and the second sterilization cycle.

9. The method of validation according to claim 7, characterized in that environment conditions of the routine cycle are identical or as close as possible to environment conditions during contamination of the container between the first sterilization cycle and the second sterilization cycle.

10. The method of validation according to claim 7, characterized in that the environment conditions include at least one selected from the group of time, temperature and pressure.

* * * * *